United States Patent
Nelson et al.

(10) Patent No.: US 8,921,072 B2
(45) Date of Patent: Dec. 30, 2014

(54) METHODS TO GENERATE DNA MINI-CIRCLES

(75) Inventors: John Richard Nelson, Clifton Park, NY (US); Nichole Lea Wood, Niskayuna, NY (US); Gregory Andrew Grossmann, Halfmoon, NY (US); Robert Scott Duthie, Schenectady, NY (US)

(73) Assignee: General Electric Compnay, Niskayuna, NY (US)

( * ) Notice: Subject to any disclaimer, the term of this patent is extended or adjusted under 35 U.S.C. 154(b) by 917 days.

(21) Appl. No.: 12/202,644

(22) Filed: Sep. 2, 2008

(65) Prior Publication Data

US 2010/0055744 A1    Mar. 4, 2010

(51) Int. Cl.
*C12P 19/34* (2006.01)
*C12Q 1/68* (2006.01)

(52) U.S. Cl.
USPC ............................ 435/91.2; 435/6.1; 435/6.12

(58) Field of Classification Search
USPC ........................................ 435/6.1, 6.12, 91.2
See application file for complete search history.

(56) References Cited

U.S. PATENT DOCUMENTS

| | | | |
|---|---|---|---|
| 5,516,292 A * | 5/1996 | Steinman | 435/91.2 |
| 6,696,278 B1 | 2/2004 | Carstens | |
| 2003/0082559 A1 | 5/2003 | Beach et al. | |
| 2004/0214329 A1 | 10/2004 | Kay et al. | |

FOREIGN PATENT DOCUMENTS

| | | |
|---|---|---|
| WO | 02083889 A | 10/2002 |
| WO | 03087330 A | 10/2003 |
| WO | 2004/013350 A1 | 2/2004 |
| WO | 2004013350 | 2/2004 |
| WO | 2004096288 A | 11/2004 |
| WO | 2006003721 A | 1/2006 |
| WO | 2006/063355 A2 | 6/2006 |
| WO | 2006110680 A | 10/2006 |
| WO | 2007/018744 A2 | 2/2007 |
| WO | 2007/060764 A1 | 5/2007 |

OTHER PUBLICATIONS

Ghosh et al. Cre-IoxP biochemistry. Methods (2002) 28: 374-383.*
Jahnz et al. An ultrasensitive site-specific DNA recombination assay based on dual-color fluorescence cross-correlation spectroscopy. Nucleic Acids Research (2005) 33(6): e60 (6 pages).*
Takaaki Watanabe and Takashi Horiuchi; "A novel gene amplification system in yeast based on double rolling-circle replication"; Received Jun. 29, 2004; Accepted Nov. 11, 2004; Published online Dec. 16, 2004; The EMBO Journal (2005) 24, 190-198, doi:10.1038/sj.emboj.7600503.
PCT/EP2009/061045, Search Report with Written Opinion, Aug. 27, 2009.
F.B. Dean et. al., "Rapid Amplification of Plasmid and Phage DNA Using Phi29 DNA Polymerase and Multiply-Primed Rolling Circle Amplification," Genome Research, 2001, vol. 11, Cold Spring Harbor Laboratory Press, ISSN 1088-9051/01, pp. 1095-1099.
I. Brukner et al., "Phi29-based amplification of small genomes," Science Direct, Analytical Biochemistry, vol. 354, 2006, pp. 154-156.

* cited by examiner

*Primary Examiner* — Ardin Marschel
(74) *Attorney, Agent, or Firm* — Jennifer E. Haeckl

(57) ABSTRACT

Methods and kits for generating circular nucleic acids in a cell-free system, and uses for the generated circular nucleic acids are provided. The methods comprise in vitro amplification of a nucleic acid template comprising a recombination site to produce tandem repeat nucleic acid sequence, and employ a recombination protein to generate the circular nucleic acids from the tandem repeat nucleic acid sequence.

16 Claims, 2 Drawing Sheets

US 8,921,072 B2

METHODS TO GENERATE DNA MINI-CIRCLES

FIELD OF INVENTION

Sequence Listing

The application contains a Sequence Listing, which has been submitted via EFS-Web and is hereby incorporated by reference in its entirety. The ASCII copy, created on Feb. 3, 2010 is named 226963-1SequenceList.txt and is 1,000 bytes in size.

The invention relates generally to methods and kits for isothermal amplification of nucleic acids to form circular nucleic acid-products. Cell-free amplification methods of nucleic acids described in the present invention help avoid contamination, and generate high-quality nucleic acids desirable for DNA-based therapeutics.

BACKGROUND

Generation of high-quality circular nucleic acids is desirable for nucleic acid based therapeutic applications, research involving transformation or transduction of cell lines, and the like. For example, deoxyribonucleic acid (DNA)-based therapeutics in gene therapy, gene transfer, and DNA vaccination demand large-scale generation of DNA having stringent quality criteria in terms of high purity, potency, efficacy, and safety.

Linear DNA molecules are rapidly degraded by nucleases, limiting their use for DNA-based therapeutic applications such as vaccination. Most of the currently available DNA therapeutic applications therefore use circular nucleic acids or plasmids. Supercoiled DNA plasmids are particularly beneficial for such applications since they are not easily degraded by the nucleases. These circular nucleic acids or plasmids are usually grown in bacterial cell culture, and their purification from the bacterial cells often employ hazardous or toxic reagents. Such plasmid preparation procedures therefore carry a potential risk of contamination in terms of toxic reagents, transposes and other episomal DNA, residual host cell nucleic acids, residual host cell proteins, endotoxins, and the like. To meet the quality criteria required for nucleic acid-based therapeutics, extensive purification techniques are often required, which are laborious, time-consuming, and expensive.

Cell-free nucleic acid amplification techniques provide a viable alternative for generating high quality nucleic acids that are devoid of any bacterial contamination. Such in vitro nucleic acid amplification techniques also have significant advantages in terms of cost savings, streamlined production, and simplified purification. However, some in vitro nucleic acid amplification methods, such as polymerase chain reaction (PCR), require quick thermal cycling, and so are often not amenable for large-scale generation of high-quality nucleic acids. Moreover, PCR products, being linear DNA sequences, are rapidly degraded in a host by the action of nucleases. In contrast, isothermal nucleic acid amplification techniques such as rolling circle amplification (RCA) or strand displacement amplification (SDA) may be employed to generate high-quality nucleic acids with less effort and expense. RCA typically produces concatamers comprising linear tandem repeat units of input circular nucleic acid template sequence. These tandem repeat sequences are useful for routine molecular biology experiments such as cloning and sequencing. However, they are seldom used in nucleic acid-based therapeutics because the transformation or transfection efficiencies of these concatamers are often lower. Currently known methods used to convert concatamers to circular nucleic acids (mini-circles) require multiple steps involving multiple enzymatic reactions. For example, concatamers may be first cut into small fragments using restriction enzymes, and then re-ligated using ligases to generate circular nucleic acids. There exists a need for efficient methods for large-scale production of high-quality circular nucleic acids that are optimally free of any bacterial sequences and contaminants.

BRIEF DESCRIPTION

One or more of the embodiments of the present invention provides methods and kits for generating circular nucleic acids in a cell-free system. In some embodiments, the methods for generating circular nucleic acid comprise methods for nucleic acid amplification. In some embodiments, the method for nucleic acid amplification comprises the steps of providing a nucleic acid template, wherein the nucleic acid template comprises a recombination site; amplifying the nucleic acid template to form a tandem repeat nucleic acid sequence comprising the recombination site; and incubating the tandem repeat nucleic acid sequence with a recombination protein to generate a circular nucleic acid. In one embodiment, the recombination site in the nucleic acid template comprises a site-specific recombination site. In one example embodiment, the site-specific recombination site in the nucleic acid template comprises a loxP site. In one embodiment, the recombination protein is chosen from Cre recombinase, bacteriophage lambda integrase, yeast Flp recombinase, or bacterial XerCD recombinase.

In some embodiments, methods for generating circular nucleic acids in a cell-free system are provided. In one embodiment, the method comprises the steps of incubating a circular nucleic acid template, wherein the circular nucleic acid template is engineered to comprise a recombination site. The method comprises the step of amplifying the circular nucleic acid template by rolling circle amplification to form a concatamer, wherein the concatamer comprises tandem repeat units of the circular nucleic acid template sequence, comprising the recombination sites. The method further comprises the step of incubating the concatamer with a recombination protein to generate the circular nucleic acids.

In some embodiments, methods for generating a nucleic acid vaccine are provided. In one embodiment, the method comprises the steps of providing a nucleic acid template comprising, a recombination site, amplifying the nucleic acid template to form a tandem repeat nucleic acid sequence comprising the recombination site, and incubating the tandem repeat nucleic acid sequence with a recombination protein to generate a nucleic acid vaccine.

In some embodiments, kits for generating circular nucleic acids in a cell-free system are provided. In one embodiment the kit comprises a Phi29 DNA polymerase and a recombination protein. In one example embodiment, the kit comprises the recombination protein chosen from Cre recombinase, bacteriophage lambda integrase, yeast Flp recombinase, or bacterial XerCD recombinase. In one example embodiment, the kit further comprises an exonuclease.

BRIEF DESCRIPTION OF DRAWING FIGURES

These and other features, aspects and advantages of the present invention will become better understood when the following detailed description is read with reference to the accompanying figures.

DETAILED DESCRIPTION

Figure 1:
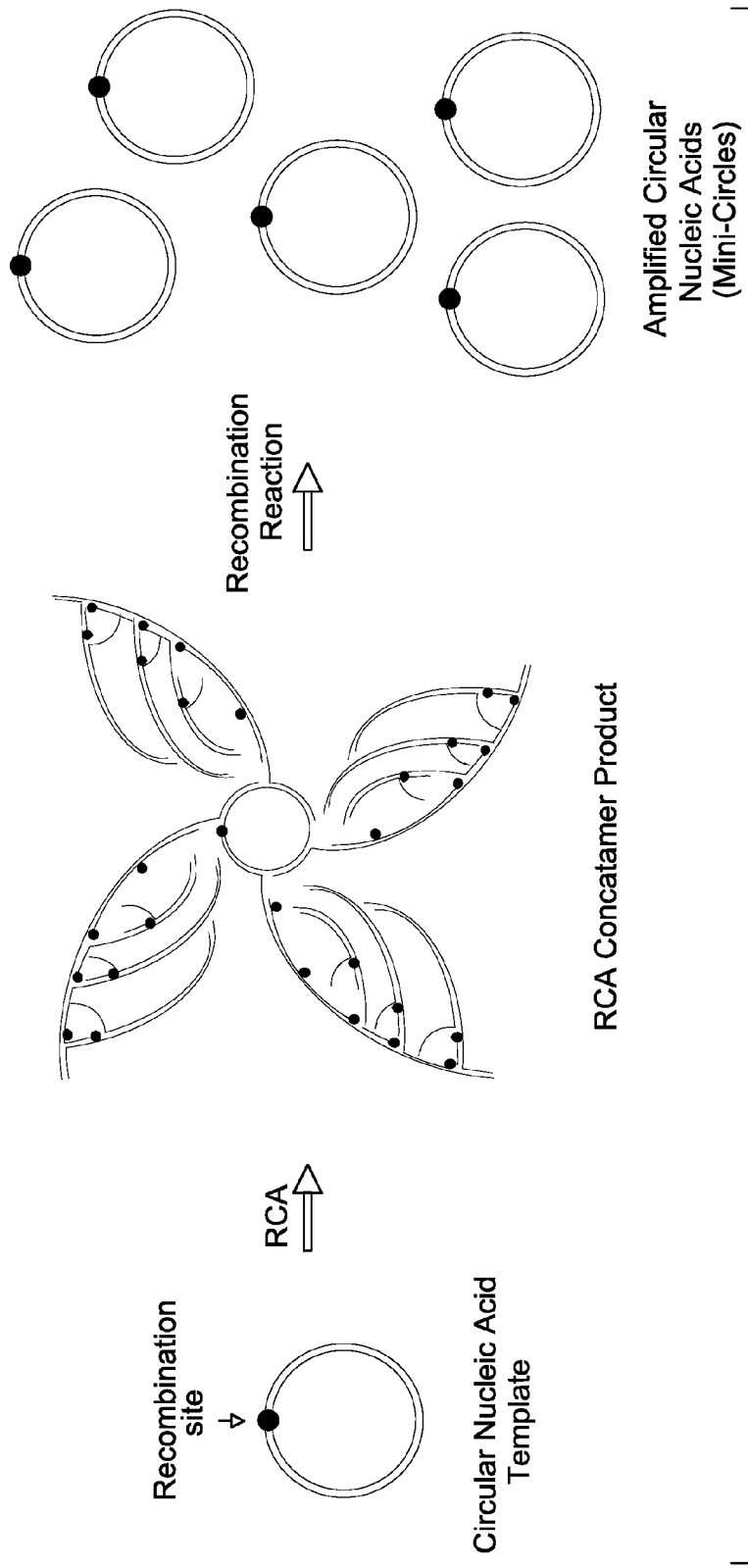
FIG. 1 is a schematic illustration of a method for generation of a circular nucleic acid according to one embodiment of the invention.

To more clearly and concisely describe and point out the subject matter of the claimed invention, the following definitions are provided for specific terms, which are used in the following description and the appended claims. Throughout the specification, exemplification of specific terms should be considered as non-limiting examples. The precise use, choice of reagents, choice of variables such as concentration, volume, incubation, time, incubation temperature, and the like may depend in large part on the particular application for which it is intended. It is to be understood that one of skill in the art will be able to identify suitable variables based on the present disclosure. It will be within the ability of those skilled in the art, however, given the benefit of this disclosure, to select and optimize suitable conditions for using the methods in accordance with the principles of the present invention, suitable for these and other types of applications.

In the following specification, and the claims that follow, reference will be made to a number of terms that have the following meanings. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term.

As used herein, the term "incubating" refers to the process of keeping a solution or a reaction mixture at a pre-determined temperature and pressure for a pre-determined period of time to achieve a specific reaction. The temperature and the period of incubation are suitably selected such that the purpose of the incubation (e.g., generation of circular nucleic acid) is achieved at the end of incubation. The incubation time and temperature may vary depending on the kinetic properties of the reagents/enzyme that are involved in the reaction.

As used herein the term "reaction mixture" refers to the combination of reagents or reagent solutions, which are used to carry out one or more chemical analyses or biological assays. In some embodiments, the reaction mixture comprises all necessary components to carry out a DNA synthesis/amplification reaction. In some embodiments, the reaction mixture includes all necessary components to circularize tandem repeat nucleic acid sequences.

As used herein, the term "amplification" or the term "amplifying" refers to the production of multiple copies of a nucleic acid template, or the production of multiple nucleic acid sequence copies that are complementary to the nucleic acid template.

As used herein, the term "nucleotide" refers to both natural and modified nucleoside phosphates. The term "nucleoside" refers to a compound having a purine, deazapurine, pyrimidine or a modified base linked at the 1' position or at an equivalent position to a sugar or a sugar substitute (e.g., a carbocyclic or an acyclic moiety). The nucleoside may contain a 2'-deoxy, 2'-hydroxyl or 2',3'-dideoxy forms of sugar or sugar substitute as well as other substituted forms. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleoside triphosphate (dNTP). Deoxyribonucleoside triphosphate may be, but is not limited to, a deoxyriboadenosine triphosphate (2'-deoxyadenosine 5'-triphosphate or dATP), a deoxyribocytosine triphosphate (2'-deoxycytidine 5'-triphosphate or dCTP), a deoxyriboadenosine triphosphate (2'-deoxyguanosine 5'-triphosphate or dGTP) or a deoxyribothymidine triphosphate (2'-deoxythymidine 5'-triphosphate or dTTP).

The term "oligonucleotide", as used herein, refers to oligomers of nucleotides or derivatives thereof. Throughout the specification, whenever an oligonucleotide is represented by a sequence of letters, the nucleotides are in 5'→3' order from left to right. In the letter sequence, letter A denotes adenosine, C denotes cytosine, G denotes guanosine, T denotes thymidine, W denotes A or T, and S denotes G or C. N represents a random nucleic acid base (e.g., N may be any of A, C, G, U, or T). A synthetic, locked, random nucleotide is represented by +N and a phosphorothioate modified random nucleotide is represented by *N.

"Nucleic acid," or "oligonucleotide", as used herein, may be a DNA, or a RNA, or its analogue (e.g., phosphorothioate analog). Nucleic acids or oligonucleotides may also include modified bases, backbones, and/or ends. Non-limiting examples of synthetic backbones include phosphorothioate, peptide nucleic acid, locked nucleic acid, xylose nucleic acid, or analogs thereof that confer stability and/or other advantages to the nucleic acids.

As used herein, the term "plasmid" or "plasmid DNA" refers to an extra-chromosomal nucleic acid that is separate from the chromosomal nucleic acid. Plasmid DNA may be capable of replicating independently of the chromosomal nucleic acid (chromosomal DNA) in a cell. Plasmid is often circular and double-stranded.

As used herein, the term "expression cassette" refers to a nucleic acid sequence comprising a nucleic acid sequence of particular interest. For example, the expression cassette may comprise one or more genes, and nucleic acid sequences for controlling their expression. The expression cassette may often comprise a promoter sequence and an open reading frame. It may also include a 3' un-translated region that, in eukaryotes, usually contains a polyadenylation site. Different expression cassettes may be transformed, transfected or transduced into different organisms including bacteria, yeast, plants, or mammalian cells as long as the correct regulatory sequences are used. In each successful transformation, the expression cassette may direct the cell's machinery to make a RNA and/or a protein.

As used herein, the term "primer" refers to a short linear oligonucleotide that hybridizes to a nucleic acid template (e.g., a DNA template to be amplified). Primers may be specific primers or random primers. The specific primers are designed to have a sequence, which is a reverse complement of a pre-determined region of the nucleic acid template to which it anneals. Both the upper and lower limits of the length of the primer are empirically determined. The lower limit on primer length is the minimum length that is required to form a stable duplex upon hybridization with the nucleic acid template. Very short primers (usually less than 3 nucleotides long) do not form thermodynamically stable duplexes with the nucleic acid template under hybridization conditions. The upper limit is determined by the possibility of having a duplex formation in a region other than the pre-determined nucleic acid sequence in the nucleic acid template. Suitable primer lengths may be in a range of about 3 to about 100 nucleotides long. Suitable primer lengths may be about 3 to about 40 nucleotides long, or may be about 3 to about 25 nucleotides long. In some embodiments, suitable primers are hexamers that are 6 nucleotides in length.

As used herein the term "DNA polymerase" refers to any enzyme that catalyzes the production or synthesis of a new DNA. DNA polymerase uses an existing DNA or RNA as a template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a nucleoside triphosphate (NTP) or deoxyribonucleoside triphosphate (dNTP) to the 3'-hydroxyl group of a growing oligonucleotide chain. This results in elongation of the new strand in a 5'→3' direction. DNA polymerase can only add a nucleotide onto a pre-existing 3'-OH group. So, to begin a DNA synthesis reaction, a DNA polymerase needs a primer at which it can add the first nucleotide. Suitable primers comprise RNA and DNA.

As used herein the term "proofreading DNA polymerase" refers to any DNA polymerase that is capable of correcting its errors while performing DNA synthesis. Proofreading DNA polymerase possesses a 3'→5' exonuclease activity apart from its polymerase activity, and this exonuclease activity is referred here as proofreading activity. Proofreading activity of such polymerases correct mistakes in the newly synthesized DNA. During DNA synthesis, when an incorrect base pair is recognized, the proofreading DNA polymerase reverses its direction by one base pair of DNA. The 3'→5' exonuclease activity (proofreading activity) of the enzyme allows the incorrect base pair to be excised. Following base excision, the polymerase re-inserts the correct base and DNA synthesis continues. When free dNTPs are present in the solution or reaction mixture suitable for DNA synthesis, the primary activity of the proofreading DNA polymerase, is DNA synthesis. However, when dNTPs are not available for DNA synthesis reaction, the primary activity of the proofreading DNA polymerase may be its 3'→5' exonuclease activity. Some of the proofreading DNA polymerases may require the presence of a divalent cation for their proofreading activity as well as for their polymerase activity. Suitable divalent cations that can switch on the proofreading activity of the proofreading polymerases include, but are not limited to, magnesium or manganese.

As used herein, the terms "reagent solution" or "solution suitable for performing a DNA synthesis reaction" refer to any or all solutions, which are typically used to perform an amplification reaction or DNA synthesis. It includes, but is not limited to, solutions used in isothermal DNA amplification methods, solutions used in PCR amplification reactions, or the like. The solution suitable for DNA synthesis reaction may comprise buffer, salts, and/or nucleotides. It may further comprise primers and/or a DNA template to be amplified.

As used herein, the term "recombination protein" refers to a protein capable of mediating recombination, for example, a recombinase. The recombination protein may mediate either a homologous recombination or a non-homologous recombination, or both. Non limiting examples of recombination protein includes the integrase family of DNA recombinases such as Cre recombinase from bacteriophage P1, bacteriophage lambda integrase, yeast Flp recombinase, bacterial XerCD recombinase, or the like.

As used herein, the term "loxP site" (locus of X-over P1) or "loxP recombination site" refers to a sequence that is recognized specifically by a Cre recombination protein or Cre recombinase. LoxP site may be a wild type loxP site or a modified loxP site. The wild type loxP site comprises a 34 base pair (bp) sequence comprising two 13 bp inverted repeats (palindromes) flanking an 8 bp asymmetric core sequence (spacer) region, which confers directionality (SEQ. ID. NO: 1). Recombination exchange takes place at the asymmetric core sequence. One Cre recombinase molecule binds to each palindrome sequence. In the wild type loxP site, strand cleavage positions are after the first, and before the last, base of the 8-bp asymmetric core.

As used herein, the term "recombination site" refers to a location in a nucleic acid sequence wherein the likelihood of a recombination event is higher than normal. The recombination site comprises nucleic acid sequences that are favorable for recombination. As used herein, the term "site-specific recombination site" refers to a recombination site comprising specific sequences, which is recognized by a specific recombination protein. For example, a site-specific recombination site may comprise a loxP site. A Cre recombination protein specifically recognizes two separate loxP sites in a nucleic acid sequence and brings about recombination between those sites.

As used herein, the term "Cre recombination protein" or "Cre recombinase" or "Cre" (cyclization recombination) refers to a site-specific recombination protein that recognizes a loxP site, and catalyzes a site-specific recombination of nucleic acid. The Cre recombinase is a member of the integrase family of DNA recombinases. It is a 34 kDa protein, comprising 4 subunits and two domains (a larger carboxyl (C-terminal) domain, and a smaller amino (N-terminal) domain). The C domain comprises a catalytic site of the enzyme. Cre recombinase recombines specific sequences of DNA without the need for any cofactors. The loxP site comprises a 34 base pair (bp) DNA sequence comprising two 13 bp inverted repeats (palindromes) flanking an 8 bp core sequence region, (spacer), which confers directionality. Recombination products may vary depending on the number, location, and relative orientation of the loxP sites. Depending on the orientation of loxP sites with respect to one another, Cre recombinase may excise, exchange, integrate, or invert DNA sequences. Two Cre recombinases bind to each loxP site, one on each half of the palindrome. The DNA bound Cre recombinases thus forms a tetrameric complex and brings two loxP sites into proximity. The Cre-mediated strand cleavage and exchange between the loxP sites occurs following the first bases and before the last base of the 8 bp core region. Cre recombinase catalyzes both inter-molecular DNA exchanges and intra-molecular excision or inversion. For example, two DNA molecules containing single loxP sites may be fused. In contrast, if two loxP sites are located in the same DNA molecule in the same orientation (co-aligned), Cre-mediated recombination preferentially excises the DNA sequence between the loxP sites and circularizes the excised DNA sequence. Even though Cre also catalyzes the reverse reaction, i.e., integration of DNA into a single loxP site, the integration is often inefficient since the inserted DNA is immediately flanked by two loxP sites, which permits re-excision. This makes the Cre-mediated excision effectively irreversible. When two loxP sites are in opposite orientation, Cre-mediated recombination lead to the inversion of the DNA sequence between the loxP sites with respect to the rest of the DNA.

One or more embodiments are directed to methods for generation of circular nucleic acids. Circular nucleic acids are generated employing a cell-free amplification system. These cell-free amplification methods yield high-quality circular nucleic acids devoid of any bacterial contamination. Generation of such high-quality circular nucleic acid may be desired in applications such as research, analytical, diagnostic, prognostic or forensic applications, and the like. Cell-free generation of circular nucleic acids may be particularly desirable if the resulting nucleic acids are to be used for therapeutic applications, for example, for generation of a DNA vaccine.

One or more embodiments of the methods for amplification of nucleic acid and subsequent generation circular nucleic acid generally comprise the steps of amplifying a nucleic acid template to generate aft amplified nucleic acid, and conversion of the amplified nucleic acid to a circular nucleic acid. In some embodiments, the amplified nucleic acid is engineered to comprise recombination sites. The amplified nucleic acid comprising the recombination sites is then converted to circular nucleic acids by a recombination protein-mediated nucleic acid recombination. In some embodiments, the amplified nucleic acid comprising the recombination sites may be generated by selecting a nucleic acid template comprising the recombination site, and amplifying the selected nucleic acid template. In other embodiments, a nucleic acid template may be engineered to comprise a recombination site, and amplifying the engineered nucleic acid template generates the amplified nucleic acid comprising the recombination sites. Engineering of the nucleic acid template may be achieved by any of the genetic engineering or molecular biology techniques known in the art, such as, but not limited to, cloning. In some embodiments, the recombination site may be a site-specific recombination site, and the recombination protein that is used to generate the circular nucleic acid from the amplified nucleic acid may be a site-specific recombinase.

The nucleic acid template may be a single-stranded nucleic acid template of it may be a double-stranded nucleic acid template. The nucleic acid template may comprise a deoxyribonucleic acid (DNA) or a ribonucleic acid (RNA). The nucleic acid template may be a synthetic nucleic acid or a natural nucleic acid. The nucleic acid template may also comprise modified nucleotides. The nucleic acid template may be a circular nucleic acid template or it may be a linear nucleic acid template. In some embodiments, the nucleic acid template is a circular nucleic acid template. In some example embodiments, a linear nucleic acid template is circularized to generate the circular nucleic acid template. In one example embodiment, the circularization of the linear nucleic acid template is effected by an enzymatic reaction, for example, by incubation with a ligation enzyme such as DNA ligase.

In some example embodiments, the nucleic acid template is engineered to comprise a loxP recombination site. In one example embodiment, the nucleic acid template is engineered to comprise a wild type loxP recombination site. In other embodiments, the nucleic acid template is engineered to comprise a mutant loxP recombination site that can be recognized by a Cre recombinase. The nucleic acid template comprising the loxP recombination site is subsequently amplified to generate an amplified nucleic acid comprising the loxP recombination sites. The loxP recombination sites in the amplified nucleic acid may be arranged in a unidirectional manner (co-aligned or arranged in same orientation). The amplified nucleic acid comprising the loxP recombination sites is then incubated with a Cre recombinase. The Cre recombinase mediates an intra-molecular excision reaction wherein the nucleic acid sequence between the loxP recombination sites are excised. The Cre recombinase subsequently circularizes the excised nucleic acid sequence to generate circular nucleic acids. In one example embodiment, the Cre recombinase used for generation of circular nucleic acids is a 38 kDa product of bacteriophage P1 cre gene.

The nucleic acid template may be amplified using any of a variety of nucleic acid amplification methods. In some embodiments, the amplification of the nucleic acid template may be performed using thermal cycling methods, such as polymerase chain reaction (PCR). In some embodiments, the nucleic acid template may be amplified using isothermal nucleic acid amplification methods. Non-limiting examples of nucleic acid amplification methods that could be used in the present invention include, ligase chain reaction (LCR), self-sustained sequence replication (SSR), nucleic acid sequence-based amplification (NASBA), loop-mediated isothermal amplification (LAMP), amplification with Qb-replicase, or the like. In some example embodiments, the nucleic acid template is amplified using strand displacement amplification reaction (SDA). In other example embodiments, the nucleic acid template is amplified using multiple displacement amplification (MDA). In some specific embodiments, the nucleic acid template is amplified using rolling circle amplification (RCA) method. Rolling circle amplification that could be used in the present invention may be a linear RCA (LRCA) or it may be an exponential RCA (ERCA). In some example embodiments, multiply primed rolling circle amplification (MPRCA) is employed for amplifying the nucleic acid template.

In some embodiments, the nucleic acid template is amplified to generate an amplified nucleic acid, in a solution suitable for performing a nucleic acid amplification reaction. The amplification reaction often employs reagents such as a primer, a nucleic acid polymerase, and free nucleotides (for example, deoxyribonucleoside triphosphates (dNTPs)). The nucleic acid polymerase that is employed in the amplification reaction may be a proofreading nucleic acid polymerase. In some embodiments, each of the reagents used in the nucleic acid amplification reaction may be pre-treated to remove any contaminating nucleic acid sequences. In some embodiments, the pre-treatment of the reagents includes incubating the reagents in presence of Ultra-Violet radiation. In some embodiments, the reagents are de-contaminated by incubating the reagents in presence of a nuclease and its co-factor (for example, a metal ion). Suitable nucleases include, but are not limited to, exonucleases such as exonuclease I or exonuclease III. Proofreading DNA polymerases that may be used in a DNA amplification reaction may be de-contaminated by incubating with a divalent metal ion (for example, magnesium or manganese). The free nucleotides employed in nucleic acid template amplification may include natural nucleotides (for example, dATP, dGTP, dCTP or dTTP) or their modified analogues. Other components such as buffers, salts and the like may also be added to allow the nucleic acid amplification to occur efficiently.

In some embodiments, amplification of the nucleic acid template, and the circularization of the amplified nucleic acid template to generate circular nucleic acids (for e.g., a recombination reaction) are performed in a single vessel. The amplification reaction and the recombination reaction may be performed sequentially or they may be performed simultaneously. For example, reaction mixture, for nucleic acid amplification may also comprise reagents required for the circularization of amplified nucleic acids. The methods for nucleic acid amplification and generation of circular nucleic acids may either be manually performed or be automated. In some embodiments, some steps of the methods may be manually performed while other steps may be automated.

In one embodiment of the method for nucleic acid amplification, the method comprises the steps of providing a nucleic acid template, amplifying the nucleic acid template to form a tandem repeat nucleic acid sequence, and incubating the tandem repeat nucleic acid sequence with a recombination protein to generate a circular nucleic acid. In one embodiment, the nucleic acid template-comprises a recombination site.

The nucleic acid template may comprise a deoxyribonucleic acid (DNA) or a ribonucleic acid (RNA). The nucleic acid template may be a single-stranded nucleic acid template or it may be a double-stranded nucleic acid template. The nucleic acid template may be a synthetic nucleic acid or a natural nucleic acid. The nucleic acid template may also comprise modified nucleotides.

In some embodiments, the nucleic acid template may be engineered to comprise a recombination site. Engineering of the nucleic acid template may be achieved by a variety of the genetic engineering or molecular biology techniques. The recombination site may be a homologous, recombination site, or it may be a non-homologous recombination site. In some embodiments, the recombination site may be a site-specific recombination site. Non-limiting examples of site-specific recombination sites that may be used comprise a loxP site, an attB site, or an attP site. In some embodiments, the nucleic acid template comprises multiple site-specific recombination sites. In some embodiments, the multiple site-specific recombination sites may result from multiple occurrences of one and the same recombination site. In other embodiments, the multiple site-specific recombination sites may result from one or more occurrences of two or more different site-specific recombination sites. For example, in some embodiments, the nucleic acid template may comprise two or more loxP sites. In other embodiments, the nucleic acid template may comprise an attB site and an attP site. In yet other embodiments, the nucleic acid template may comprise one or more loxP sites, and one or more attB sites, and/or attP sites. In some embodiments, the multiple site-specific recombination sites in the nucleic acid template may be arranged in a unidirectional (arranged in same orientation, or co-aligned) manner. In other embodiments, some of the multiple site-specific recombination sites in the nucleic acid template may be arranged in a unidirectional manner, while others may be arranged in the opposite orientation. In some embodiments, these site-specific recombination sites are recognized by a unidirectional, site-specific recombination protein. Suitable site-specific recombination proteins that may be used with the present invention includes, but not limited to, a Cre recombinase, a bacteriophage lambda integrase, yeast Flp recombinase, or bacterial XerCD recombinase. In some embodiments, the recombination protein comprises a Cre recombinase from bacteriophage P1. The selection of appropriate recombination protein is primarily determined by the sequence and/or orientation of the recombination site.

In one example embodiment, the nucleic acid template is a deoxyribonucleic acid (DNA) template. The DNA template may comprise a genomic DNA or a cDNA. The DNA template may be a circular DNA template, a linear DNA template, or a nicked DNA template. In some embodiments, the nucleic acid, template is a circular DNA template, and methods may be used to amplify the circular DNA template to generate multiple copies of the circular DNA (DNA mini-circles) in a cell-free system. In some embodiments, the circular DNA template comprises a recombination site. In such embodiments, the method may comprise in vitro amplification of the circular DNA template comprising the recombination site to produce a tandem repeat DNA sequence. The produced tandem repeat sequence comprises a plurality of the recombination sites. The method may further comprise the treating the tandem repeat nucleic acid sequence with a recombination protein to generate multiple copies of the circular DNA from the tandem repeat DNA sequence.

In some embodiments, the nucleic acid template is a circular DNA template. A variety of methods may be used to prepare a circular DNA template for use with methods of the invention. In some embodiments, a linear DNA template may be circularized to generate the circular DNA template. In one example embodiment, the circularization of the linear DNA template may be effected by an enzymatic reaction, for example, by incubation with a ligation enzyme such as DNA ligase. In some embodiments, the terminal ends of the linear DNA template are hybridized to a nucleic acid sequence such that the terminal ends come in close proximity. Incubating with a ligation enzyme may then effect the circularization of the hybridized, linear DNA template to generate a circular DNA template. In some embodiments, a plasmid DNA may be used as a circular DNA template. In some embodiments a modified plasmid DNA lacking typical genetic sequences needed for plasmid DNA selection and replication in a bacteria may be used as the circular DNA template. In some embodiments, an existing plasmid DNA may be enzymatically modified to generate a suitable circular DNA template. For example, a restriction enzyme mediated digestion of an existing plasmid DNA followed by re-circularization may be used to generate a circular DNA template. Suitable circular DNA template, may also be generated by PCR amplification of a portion of a larger DNA (for example, a genomic DNA, or a DNA from a DNA library) using appropriate PCR primers, followed by circularization of the PCR product. Circular DNA templates may also be generated by chemical synthesis of suitable linear oligonucleotides followed by circularization of the synthesized oligonucleotide. In some embodiments, the synthesized linear oligonucleotides may comprise appropriately positioned recombination sites to achieve circularization via recombinase-mediated DNA recombination to generate circular DNA templates.

In some embodiments, the circular DNA template may be engineered to comprise a recombination site. Engineering of the circular DNA template may be achieved by any of the genetic engineering or molecular biology techniques. The recombination site may be a homologous recombination site, or it may be a non-homologous recombination site. In some embodiments, the recombination site may be a site-specific recombination site. Non-limiting examples of site-specific recombination sites that may be used comprise a loxP site, an attB site, or an attP site. In some embodiments, the circular DNA template comprises multiple site-specific recombination sites. In some embodiments, the multiple site-specific recombination sites may result from multiple occurrences of one and the same recombination site. In other embodiments, the multiple site-specific recombination sites may result from one or more occurrences of two or more different site-specific recombination sites. For example, in some embodiments, the circular DNA template may comprise two or more loxP sites. In other embodiments, the circular DNA template may comprise an attB site and an attP site. In yet other embodiments, the circular DNA template may comprise one or more loxP sites, one or more attB sites, and/or one or more attP sites. In some embodiments, the multiple, site-specific recombination sites in the circular DNA template may be arranged in a unidirectional (arranged in same orientation or co-aligned) manner. In some embodiments, these site-specific recombination sites are recognized by a unidirectional, site-specific recombinase.

In some embodiments, the circular DNA template is engineered to comprise a delivery unit. In some embodiments, recombination sties may flank the delivery unit. In some embodiments, the delivery unit may comprise an expression cassette.

In some embodiments, the circular DNA template is engineered to comprise an expression cassette, wherein recombination sites flank the expression cassette. In some embodiments, the expression cassette may be a eukaryotic expression cassette. The expression cassette may comprise a nucleic acid sequence of particular interest. The nucleic acid sequence of particular interest may be, for example, but not limited to, an intact gene, or a gene fragment. In some embodiments, the expression cassette may also comprise a transcription initiation and a transcription termination sequence. In some embodiments, the expression cassette may further comprise genetic elements or sequences that may be needed for expression (for example, a promoter sequence or enhancer sequence) of the nucleic acid sequence of particular interest (e.g. a gene), and processing (e.g., processing a signaling sequence) of the expressed product in a host. Suitable hosts include, but not limited to, rodents (e.g., mouse, rat), vertebrates (chicken), invertebrates, primates (e.g., monkey), or mammals (e.g., rabbit, cat, dog, pig, cow, horse, human). In some embodiments the expression cassette comprises a gene of interest, and genetic elements or sequences that may be needed for expression of the gene of interest and processing of the expressed gene product in humans.

In some embodiments, the expression cassette comprises a nucleic acid sequence that can be transcribed to an RNA. The nucleic acid sequence in the expression cassette may be selected to yield an RNA (e.g., miRNA, siRNA) that may be employed for RNA-based therapeutics or RNA-based cellular modifications. For example, the expression cassette may comprise a nucleic acid sequence, which when transcribed, may yield a small interfering RNA (siRNA) or a micro RNA (miRNA).

In some example embodiments, the site-specific recombination site in a circular DNA template comprises a loxP site. The circular DNA may further comprise an expression cassette. The expression cassette may comprise a gene of interest. It may also comprise genetic elements or sequences that may be needed for expression of the gene of interest and processing of the expressed gene product in a host, for example, a human. In some embodiments, the expression cassette comprises stabilizing sequences that facilitate rapid uptake and/or prolong longevity of expression of the cassette once inside the cell. In some embodiments the expression cassette is a eukaryotic expression cassette comprising a gene that encodes a polypeptide. In some embodiments, the encoded polypeptide may be capable of generating an immune reaction in the host. In some embodiments, the gene encodes a polypeptide that may generate an immune response in human.

In some example embodiments, the circular DNA template comprises two loxP sites flanking an expression cassette, wherein the loxP sites are aligned in the same direction (co-aligned). In some embodiments, the expression cassette flanked by the loxP sites comprises a gene of interest. In some embodiments the expression cassette flanked by the loxP sites comprises a gene of interest, and genetic elements or sequences that may be needed for expression of the gene of interest, and processing of the expressed gene product in humans. In some example embodiments, the circular DNA template comprises two unidirectional loxP sites flanking a eukaryotic expression cassette, wherein the eukaryotic expression cassette comprises a gene that encodes a polypeptide capable of generating an immune reaction in a host, for example, human. In such embodiments, the method comprises in vitro amplification of the circular DNA template comprising the loxP sites to produce a tandem repeat DNA sequence. In some embodiments, the amplification is achieved by using rolling circle amplification (RCA). The produced tandem repeat sequence comprises a plurality of the co-aligned loxP sites, wherein two co-aligned loxP sites flank the expression cassette. The incubation of the tandem repeat nucleic acid sequence with a recombination protein then excises (loops out) the expression cassette in the form of a circular DNA (mini-circle).

The DNA template may be amplified using any of a variety of DNA amplification methods. In some embodiments, the amplification of the DNA template may be performed using thermal cycling methods, such as polymerase chain reaction (PCR). In some embodiments, the DNA template may be amplified using isothermal DNA amplification methods. Non-limiting examples of DNA amplification methods comprise ligase chain reaction (LCR), self sustained sequence replication (SSR), nucleic acid sequence-based amplification (NASBA), loop-mediated isothermal amplification (LAMP), and amplification with Qb-replicase. In some example embodiments, the DNA template is amplified using strand displacement amplification reaction (SDA). In some other example embodiments, the DNA template is amplified using multiple displacement amplification (MDA). In some specific embodiments, the DNA template is amplified using rolling circle amplification (RCA).

In embodiments wherein DNA template comprises a recombination site, the amplification of the DNA template may yield a concatamer comprising tandem repeat units of the DNA template sequence. The concatamer further comprises a plurality of recombination sites. In some embodiments, the recombination sites may be suitably arranged such that the incubation of the concatamer with a recombination protein excises (loops out) the DNA sequence flanked by the recombination sites in the form of a circular DNA (mini-circle). The recombination protein that may be used includes, but not limited to, a Cre recombinase, a bacteriophage lambda integrase, a yeast Flp recombinase, or a bacterial XerCD recombinase. In some embodiments, the recombination protein comprises a Cre recombinase from bacteriophage P1. The selection of appropriate recombination protein is primarily determined by the sequence and/or orientation of the recombination site.

In some embodiments, wherein the DNA template is a circular DNA template, the circular nucleic acid template may be amplified using a rolling circle amplification method. Rolling circle amplification that may be suitable to use with the present invention includes a linear RCA (LRCA), or an exponential RCA (ERCA). In some example embodiments, multiply primed rolling circle amplification (MPRCA) is employed for amplifying the circular DNA template. In some embodiments, a ligation rolling circle amplification is employed for amplifying the circular DNA template. In some embodiments, the circular DNA template comprises a recombination site. The rolling circle amplification of the circular DNA template then yields a concatamer comprising tandem repeat units of DNA template sequence. The concatamer further comprises a plurality of recombination sites. In some embodiments, the recombination sites may be suitably arranged such that the incubation of the concatamer with a recombination protein excises (loops out) the DNA sequence flanked by the recombination sites in the form of a circular DNA (mini-circle).

The methods may further comprise incubating the reaction mixture with a nuclease. The incubation of the reaction mixture with the nuclease may be performed after the incubation with the recombination protein. Incubating the reaction mixture with the nuclease may be used to digest any residual linear nucleic acid sequences or tandem repeat sequences that may not have been circularized by the action of the recombination protein. Suitable nucleases that may be used include, but are not limited to exonuclease. The exonuclease may be a single-strand specific exonuclease or it may be a double-strand specific exonuclease. A single exonuclease or a combination of exonucleases may be used to digest residual, linear nucleic acid sequences. Suitable exonucleases that may be used include, but are not limited, to exonuclease I, exonuclease III, exonuclease VII, T7 gene-6 exonuclease, spleen exonuclease, T5 D15 exonuclease or lambda exonuclease. In one example embodiment, a combination of exonucleases, such as exonuclease I and exonuclease III, may be used.

In some embodiments, the methods may further comprise incubating the reaction mixture with a single-stranded DNA binding-protein (SSB protein). Suitable SSB proteins that may be used include, but are not limited to, extreme thermostable single stranded DNA-binding protein (ET SSB from New England Biolabs, Mass), *E. coli* RecA, RecA homolog isolated from *Thermus thermophilus* (Tth RecA from New England Biolabs, Mass.), phage T4 gene-32 protein, or *E. coli* SSB protein. The addition of the exonuclease, and the SSB protein to the reaction mixture may be performed either sequentially or simultaneously. In embodiments where the sequential addition is performed, the addition may be carried out in any particular order. For example, in some embodiments, the exonuclease may be added to the reaction mixture first followed by the SSB protein. In some other embodiments, the SSB protein may be contacted with the reaction mixture first followed by addition of the exonuclease. In yet other embodiments, the exonuclease and the SSB protein may be pre-incubated together before adding the incubated mixture to the reaction mixture.

The methods may further comprise improving the homogeneity of generated circular nucleic acids by eliminating mismatched nucleotides that resulted from errors in nucleic acid polymerization. For example, homogeneity may be improved by incubating with mutation detection enzymes (e.g., resolyase, T4 endonudease VII, or T7 endonuclease I) or other enzymes used to detect gene mutations or polymorphisms.

In one example embodiment, a method for generating circular nucleic acids in a cell-free system comprises the steps of (a) incubating a circular nucleic acid template, wherein the circular nucleic acid template is engineered to comprise a recombination site; (b) amplifying the circular nucleic acid template by rolling circle amplification to form a concatamer, wherein the concatamer comprises tandem repeat units of the circular nucleic acid template sequence comprising the recombination site; and (c) incubating the concatamer with a recombination protein to generate the circular nucleic acids.

Rolling circle amplification of the circular nucleic acid template may comprise the steps of incubating the circular nucleic acid template with a primer to form a template-primer complex. The template-primer complex may then be incubated with a nucleic acid polymerase in presence of free nucleotides to bring about amplification of the circular nucleic acid template.

Circular nucleic acid template may be a single-stranded circular nucleic acid template or it may be a double-stranded circular nucleic acid template. The circular nucleic acid template may be a circular DNA template, a circular RNA template, or a circular DNA-RNA hybrid template. The circular nucleic acid template may be a synthetic nucleic acid or a natural nucleic acid. The circular nucleic acid template may also comprise modified nucleotides or ribonucleotides. The circular DNA template may be derived from a genomic DNA, a RNA template (using reverse transcriptase enzymes) or a cDNA. In one example embodiment, the circular nucleic acid template is a deoxyribonucleic acid (DNA) template. The circular nucleic acid template may be engineered to comprise a recombination site, for example, but not limited to, a loxP site, an attB site, an attP site, or combinations thereof. In some example embodiments, the circular nucleic acid is engineered to comprise a wild type loxP recombination site (SEQ. ID. NO: 1).

The primer used in the amplification reaction typically depends on the sequence of the circular nucleic acid template to be amplified and the selected amplification method. Either a single primer or multiple primers may be used for amplification. The primer may either be a specific primer or a random primer. Specific primers have, or are engineered to have, a nucleotide sequence that is complementary, in the Watson-Crick sense, to a sequence present in the circular nucleic acid template. Use of random primer results in hybridization of the primers with the circular nucleic acid template at random locations. The random primers may also hybridize with the strand-displaced product (e.g., in a RCA reaction) at random locations. In some embodiments, the primer comprises a nuclease-resistant primer, for example, a primer resistant to an exonuclease (for example a $3' \rightarrow 5'$ exonuclease). Exonuclease-resistant primers may comprise modified nucleotides to make them resistant to the exonuclease digestion. For example, a primer may possess one, two, three or four phosphorothioate linkages between nucleotides at the 3' end of the primer sequence. The modified nucleotide may be a phosphorothioate nucleotide. The modified nucleotide may either be located, at 3'-terminal position or may be located at a position other than the 3'-terminal position. In some embodiments, a random hexamer primer is used that is resistant to $3' \rightarrow 5'$ exonuclease activity. In some embodiments, primers comprising the sequences such as WWNN*N*S or NNNN*N*N are used as a suitable primer. In these cases, the primer sequences may have two phosphorothioate nucleotides at the 3'-terminal end (* represents a phosphorothioate bond between the nucleotides). In some embodiments, multiple primers are used for the nucleic acid template amplification. In some embodiments, the multiple primers are primers that are sensitive to exonuclease activity, primers resistant to exonuclease activity, or a mixture of primers sensitive to exonuclease activity and resistant to exonuclease activity.

Rolling circle amplification of a circular DNA template may be performed by incubating the template-primer complex with a suitable DNA polymerase and free nucleotides (for example, deoxyribonucleoside triphosphates) in a solution suitable for performing a DNA synthesis reaction. The DNA polymerase may be any known prokaryotic, fungal, viral, bacteriophage, plant of eukaryotic DNA polymerase. Suitable DNA polymerases may also comprise holoenzymes, functional portions of the holoenzymes, chimeric polymerase or any modified polymerase that can effectuate the synthesis of a DNA molecule. Non-limiting examples of suitable DNA polymerases that may be used include bacteriophage Phi29 DNA polymerase, Phi29-like; polymerases (for example, Phage M2 DNA polymerase, Phage B103 DNA polymerase;

or Phage GA-1 DNA polymerase), phage Phi-PRD1 polymerase, VENT DNA polymerase, DEEP VENT DNA polymerase, KlenTaq® DNA polymerase, DNA polymerase I, DNA polymerase I modified with T7 DNA polymerase sequences, Klenow fragment of DNA polymerase I, DNA, polymerase III, DNA polymerase III holoenzymes, T5 DNA polymerase, T4 DNA polymerase holoenzymes, T7 DNA polymerase; genetically engineered T7 DNA polymerase having reduced or insignificant 3'→5' exonuclease activity (e.g., Sequenase DNA polymerase), DNA polymerase form *Thermoanaerobacter thermohydrosulfuricus* (Tts DNA polymerase), or fragment thereof, modified Tts DNA polymerase, Bst polymerase, rBST DNA polymerase, N29 DNA polymerase, or TopoTaq DNA polymerase.

The DNA polymerase that is used to amplify the circular DNA template may be, but is not limited to, a proofreading DNA polymerase of a non-proofreading DNA polymerase. In some embodiments, the proofreading DNA polymerase comprises a thermally stable DNA polymerase. Proofreading DNA polymerase may be a thermophilic DNA polymerase or a mesophilic DNA polymerase. In some embodiments, a combination of a proofreading DNA polymerase and a non-proofreading DNA polymerase may be used for efficient amplification of the DNA template. Any suitable, proofreading DNA polymerase may be used. Examples of proofreading polymerases that are suitable for use include, but are not limited to, Phi29 DNA polymerase, hi-fidelity fusion DNA polymerase (for e.g., *Pyrococcus*-like enzyme with a processivity-enhancing domain from New England Biolabs, MA), Pfu DNA polymerase from *Pyrococcus furiosus* (Strategene, Lajolla, Calif.), Klenow fragment from DNA polymerase I of *E. coli*, T7 DNA polymerase, T4 DNA polymerase, DNA polymerase from *Pyrococcus* species GB-D (New England Biolabs, MA) and DNA polymerase from *Thermococcus litoralis* (New England Biolabs, MA). Suitable examples of non-proofreading DNA polymerase that could be used include, but hot limited to Taq DNA polymerase, Tts DNA polymerase, large fragment of Bst DNA polymerase, exo (−) DNA Polymerase gene from *Pyrococcus* species GB-D (New-England Biolabs, MA), exo (−) DNA Polymerase from *Thermococcus litoralis* (New England Biolabs, MA).

In some embodiments, the methods employ a highly processive, strand-displacing, polymerase to amplify circular nucleic acid template under conditions for high fidelity base incorporation. A high fidelity DNA polymerase refers to a DNA polymerase that, under suitable conditions, has an error incorporation rate equal to or lower than those associated with commonly used thermostable PCR polymerases such as Vent DNA polymerase or T7 DNA polymerase (from about 1.5× $10^{-5}$ to about $5.7 \times 10^{-5}$). Additional enzymes may be included in the amplification reaction mixture to minimize misincorporation events. For example, protein mediated error correction enzymes, such as, MutS, may be added to improve the polymerase fidelity either during or following the polymerase reaction.

In some example embodiments, Phi29 DNA polymerase or Phi29-like polymerase are used for amplifying the circular DNA template by rolling circle amplification method. In some embodiments, a combination of a Phi29 DNA polymerase and a Taq DNA polymerase may be used for the circular DNA amplification.

During the amplification reaction, the circular nucleic acid template is replicated by a polymerase in the presence of deoxyribonucleoside triphosphates (dNTPs), or ribonucleotide triphosphates (NTPs) or their modified counterparts, forming a concatamer comprising tandem repeat unit of the circular nucleic acid template sequence. When circular nucleic acid template comprises a recombination site, the concatamer formed may comprise multiple recombination sites. When concatamers are treated with a suitable recombination protein, the recombination protein mediates nucleic acid recombination at the recombination sites of the concatamer. For example, when a circular DNA template comprises a loxP recombination site, the amplification of the circular DNA template by rolling circle amplification generates a concatamer, comprising multiple loxP sites at regular intervals (each repeat unit in the concatamer will have a loxP site). These loxP sites are arranged in the same orientation (unidirectionally arranged, or co-aligned) along the tandem repeat sequence of the concatamer. Incubation of the concatamer with a Cre recombination protein results in the excision and circularization of nucleic acid sequences that are flanked by two unidirectionally arranged loxP recombination sites. This results in the generation of multiple circular DNAs. If the recombination occurs at two consecutive, unidirectionally arranged loxP recombination sites, the generated circular DNA may comprise a single loxP recombination site. However, if the recombination occurs at non-consecutive, unidirectionally arranged loxP recombination sites, the generated circular DNA may comprise multiple loxP recombination sites, for example, the generated circular nucleic acid may contain internal loxP sites. In one example embodiment, the Cre recombination protein that is used to generate circular nucleic acids from the concatamer comprising multiple loxP sites is a 38 kDa product of bacteriophage P1 cre gene.

Suitable recombination proteins that may be used include, but are not limited to, a Cre recombinase, a bacteriophage lambda integrase, yeast Flp recombinase, or bacterial XerCD recombinase. The selection of appropriate recombination protein is primarily determined by the sequence and/or orientation of the recombination site.

Rolling circle amplification of an RNA template may be performed by employing a reverse transcriptase, a combination of reverse transcriptase and DNA polymerase, or an enzyme that has both reverse transcriptase activity and DNA polymerase activity (e.g., delta-Tts enzyme).

In some embodiments, the polymerases and other enzymes constitute soluble forms of the enzymes. However, solid phase nucleic acid amplification reactions or solid phase recombination reactions may also be employed to streamline the generation of circular nucleic acids. Fusion proteins comprising, optimal regions of different enzymes (e.g., polymerases) that are designed to improve fidelity, efficiency and processing of the final product may be used. Recombinant forms of the enzymes containing one ore more affinity tags (e.g., His-tag, S-tag, Calmodulin-binding peptide, or Protein A) may also be used. The tags may help in recovering the enzymes, immobilized on a solid matrix through the tag moiety, and may be used in subsequent enzymatic reactions.

One or more of the methods may further comprise steps of purifying, analyzing and/or quantifying the circular nucleic acids (mini-circles). Any suitable techniques that are used for purification, analysis or quantification of nucleic acids may be employed. Non-limiting examples include, filtration, affinity capture, gel electrophoresis, sequencing or HPLC analysis. For example, the purification of the circular nucleic acids may be achieved by affinity capture.

In some embodiments, the methods may further comprise processing of the generated circular nucleic acids. Post-processing of the generated nucleic acids may vary according to the intended use. In one example embodiment, the generated circular nucleic acids are processed to produce supercoiled circular nucleic acids. In some embodiments, the supercoiling may be effected by treating the generated circular nucleic acids with a nucleic acid gyrase or gyrase-like enzymes (e.g., topoisomerase II or DNA gyrase).

In some embodiments, the methods may further comprise transfecting or transducing the generated circular nucleic acids to a eukaryotic cell. In some other embodiments, the methods may further comprise transforming a prokaryotic cell using the generated circular nucleic acids. The transfection, the transduction or the transformation of the circular nucleic acid may be performed by using any suitable technique. Non-limiting examples include viral transaction methods, non-viral transfection methods (e.g., cationic lipid-based nucleic acid transfection, polymer-based transfection), electroporation, or transformation via heat shock.

Compositions, comprising circular nucleic acids generated by the methods of one or more of the embodiments may comprise the generated circular nucleic acids alone, or their derivatives that are produced by post-processing of the circular nucleic acids, or a combination. In some embodiments, the circular nucleic acid of the composition may comprise an expression cassette. In some embodiments, the expression cassette may be a eukaryotic expression cassette. The expression cassette may comprise a sequence of interest, for example, a gene. In some embodiments, the expression cassette comprises a gene that encodes a polypeptide a polypeptide, which may generate an immune response in a host (e.g., human). For example, in some embodiments, the gene may encode an antigenic or immunogenic protein.

The circular nucleic acid generated by using methods, and compositions made using the circular nucleic acids may be used in nucleic acid-based therapeutic applications such as DNA therapy. These uses may include, but are not limited to, vaccination against specific diseases (e.g., DNA vaccine), or treatment of an existing disease. The compositions may be used in therapeutics to predict, diagnose or treat a disease of a genetic disorder in a host, for example, a human, an animal or a plant.

The circular nucleic acids generated by the methods, and compositions comprising the circular nucleic acids may also be used for applications such as, but not limited to, antibody production or gene silencing. The antibodies may be produced in vivo following successful administration of the circular nucleic acids containing appropriate expression cassettes designed to prevent or treat a disease caused by a pathogen, such as an influenza virus or a human immunodeficiency virus (HIV). For example, the sequence encoding the influenza haemagglutination protein under the control of an eukaryotic promoter may be used to elicit humoral and/or cellular immune response in animals targeted by influenza A virus. Similarly, the expression of the sequence encoding a truncated HIV envelope protein may be used to induce effective immunogenic response against HIV.

In some embodiments, the circular nucleic acid comprises an expression cassette containing an antisense oligonucleotide sequence to a specific gene. Administration of such circular nucleic acid to a cell may be used to silence the protein expression of that specific gene in vivo. For example, administration of a circular nucleic acid comprising antisense oligonucleotide sequence of ICP4 or IPC47 of herpes simplex virus (HSV) may be used to modulate the protein expression in vivo. Expression of an anti-IPC4 transcript or an anti-IPC47 transcript in-vivo silences the IPC4 gene or IPC47 gene, blocks the production of IPC4 protein or IPC47 protein in the cell, and thus can minimize proliferation of the HSV virus. Suitable gene silencing target may include, but not limited to, genes of coronavirus, adenovirus, influenza virus, para-influenza virus, human papilloma virus, or rhinovirus.

The composition may further comprise components that may facilitate targeting to a particular cell or tissue, modify cellular uptake, modify therapeutic efficiency, or modify shelf-life of the circular nucleic acids. These components may either increase or decrease any/all of the properties of the composition. In some embodiments, the composition comprises components that mediate controlled release of the circular nucleic, acids. For example, biocompatible, controlled-release polymers such as poly (D,L-lactide-co-glycolide) (PGLA) microspheres, or poly(ethylene-co-vinyl acetate) (EVAc) matrices may be included in the composition to effectuate a controlled, adjustable, and predictable release of the circular nucleic acids.

In one or more of the embodiments, the methods for generating a nucleic acid vaccine comprise the steps of providing a nucleic acid template comprising a recombination site, amplifying the nucleic acid template to form a tandem repeat nucleic acid sequence comprising the recombination site, and incubating the tandem repeat, nucleic acid sequence with a recombination protein to generate a nucleic acid vaccine. In some embodiments, the nucleic acid template may further comprise an expression cassette. In some embodiments, the nucleic acid template may be a circular nucleic acid template (e.g., a circular DNA template), and the amplification of the circular nucleic acid template may be performed using rolling circle amplification. In some embodiments, a Phi29 DNA polymerase is used for amplifying the circular nucleic acid template. In some embodiments, the recombination site in the circular nucleic acid is a loxP recombination site, and the recombination protein used in the method is a Cre recombinase. In some embodiments, the method may further comprise post-processing the generated nucleic acid vaccine.

In some embodiments, a kit for generating circular nucleic acids in a cell-free system comprises reagents that are required for generating circular nucleic acid using the methods described in the present invention. In some embodiments, the kit comprises a nucleic acid polymerase and a recombination protein. The nucleic acid polymerase in the kit is capable of amplifying a nucleic acid template to generate a concatamer comprising tandem repeat unit of the nucleic acid template sequence. In some embodiments, the kit comprises a nucleic acid polymerase having strand-displacing activity and a recombination protein. The nucleic acid polymerase may be a highly processive, high fidelity nucleic acid polymerase. The recombination protein in the kit may mediate a homologous recombination or a non-homologous recombination, or both.

In some embodiments, the kit comprises a DNA polymerase. Suitable DNA polymerases that may be included in the kit include, but are not limited to, a prokaryotic, a fungal, a viral, a bacteriophage, a plant, or a eukaryotic DNA polymerase. Suitable DNA polymerases may also include, but are not limited to, holoenzymes, functional portions of the holoenzymes, or any modified polymerase that can effectuate the synthesis of a DNA molecule. Non-limiting examples of suitable DNA polymerases that the kit may comprise include, bacteriophage Phi29 DNA polymerase, Phi29-like polymerase (for example, Phage M2 DNA polymerase, Phage B103 DNA polymerase, or Phage GA-1 DNA polymerase), phage Phi-PRD1 polymerase, DNA polymerase from *Thermococcus litoralis* (VENT DNA polymerase), DNA polymerase from *Pyrococcus* species (DEEP VENT DNA polymerase), Pfu DNA polymerase from *Pyrococcus furiosus*, Tts DNA polymerase, Bst polymerase, rBST DNA polymerase, KlenTaq® DNA polymerase, *E. Coli* DNA polymerase I, DNA polymerase I modified, with T7 DNA polymerase sequence, Klenow fragment of DNA polymerase I, DNA polymerase III, DNA polymerase III holoenzymes, T5 DNA polymerase, T4 DNA polymerase holoenzymes, T7 DNA polymerase, N29 DNA polymerase, or TopoTaq DNA polymerase.

In some embodiments of the kit, the recombination protein is a site-specific recombination protein. Suitable site-specific recombination proteins include, but are not limited to, a Cre recombinase, a bacteriophage lambda integrase, yeast Flp recombinase, or bacterial XerCD recombinase. In some embodiments, the kit comprises an integrase family of DNA recombinase. In some embodiments, the recombination protein comprises a Cre recombinase from bacteriophage P1.

In one example embodiment, the kit comprises a Phi29 DNA polymerase and a Cre recombinase.

In some embodiments, the kit may further comprise a single stranded DNA-binding protein (SSB protein). Suitable SSB proteins that may be included in the kit include, but not limited to, extreme thermostable single stranded DNA-binding protein (ET SSB from New England Biolabs, MA), *E. coli* RecA, RecA homolog isolated from *Thermus thermophilus* (Tth RecA from New England Biolabs, MA), phage T4 gene-32 protein, or *E. coli* SSB protein.

In some, embodiments, the kit may further comprise a nuclease. In some embodiments, the kit comprises an exonuclease. Non-limiting examples of suitable exonucleases that the kit may comprise include exonuclease I, exonuclease III, exonuclease VII, T7 gene-6 exonuclease, spleen exonuclease, T5 D15 exonuclease, or lambda exonuclease. In some embodiments, the kit comprises exonuclease III. In some embodiments, the kit comprises a combination of exonucleases. In some example embodiments, the kit comprises a mixture of exonuclease I and exonuclease III. The combination of exonucleases may be provided in the kit in a single vessel or it may be provided in multiple vessels.

The kit may further comprise a nucleic acid vector. The nucleic acid vector may comprise a recombination site. In some embodiments, the recombination site in the nucleic acid vector may be site-specific recombination site. Non-limiting examples of site-specific recombination sites that may be present in the nucleic acid vector include a loxP site, an attB site, or an attP site. The nucleic acid vector may further comprise suitable sequences that may be recognized by a restriction enzyme. In some embodiments, the nucleic acid vector may comprise an expression cassette. The expression cassette may comprise a gene of interest. The expression cassette may be a eukaryotic expression cassette comprising a gene that encodes a polypeptide. In some embodiments, the encoded polypeptide may be capable of generating an immune reaction in the host. The gene of interest may encode a polypeptide that may generate an immune response in human. The nucleic acid vector may further comprise genetic elements or sequences that may be needed for expression of the gene of interest and processing of the expressed gene product in a host such as a human.

The kit may further comprise a buffer solution that may be suitable for performing a nucleic acid amplification reaction and/or a recombination reaction. The kit may comprise a buffer solution that is pre-made or it may comprise reagents needed to generate the buffer solution.

The kit may further include an instruction manual detailing the specific components included in the kit. The kit may also include an instruction manual detailing the protocols for using the components in the kit for the methods described in the present invention.

The methods may be adapted for semi-automated or fully automated platform, and/or for large-scale generation of the circular nucleic acids. Scale-up may be accomplished by increasing the number of reactions while keeping each reaction volume relatively small (e.g., <1 mL) whereby the nucleic acid template is amplified simultaneously using multi-well plates in standard or custom-built platforms. Alternatively, scale-up may involve larger volumes to generate large quantities of the circular nucleic acids in a single reaction. Multiple platforms of mixed capacities may be arranged in parallel and may be arranged to function in a coordinate manner as a part of a larger bio-manufacturing facility.

EXAMPLES

Unless specified otherwise, ingredients described in the examples are commercially available from common chemical suppliers. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "μL": microliters; "min.": minutes and "h.": hours.

FIG. 1 is a schematic representation of one of the general embodiments of the present invention. A circular nucleic acid template (input) comprising a recombination site is amplified by using rolling circle amplification (RCA) followed by a recombination reaction to generate nucleic acid mini-circles. The amplification reaction generates a concatamer product comprising tandem repeat units of the circular nucleic acid template sequence. FIG. 1 illustrates the formation of a branched RCA concatamer product from a multiply primed, exponential rolling circle amplification. The concatamer product thus comprises a plurality of recombination sites, which may be aligned in a unidirectional manner (co-aligned). The concatamer product is then treated with a recombination protein that loops out the nucleic acid sequences that are flanked by recombination sites, to generate multiple copies of the input circular nucleic acid template.

Example 1

The effect of processing of RCA products with a recombination protein on the efficiency of bacterial transformation is illustrated in the following example. A plasmid vector, pUC18, and an engineered plasmid construct, pUC/loxP (DNA templates) were independently amplified by RCA using bacteriophage Phi29 DNA polymerase. A loxP DNA sequence (SEQ. ID. NO: 1) was engineered into the plasmid vector pUC18 to generate the plasmid construct, pUC/loxP. The amplified nucleic acids were then treated with a Cre recombinase. The treated, amplified nucleic acids were then transformed into a bacterium, and the transformation efficiency was quantified.

RCA of a circular nucleic acid template (plasmids; pUC18 or pUC/loxP) yields a high molecular weight, hyper-branched concatamer comprising tandem repeat units of the circular nucleic acid sequence (RCA products; pUC18-RCA or pUC/loxP-RCA). When the nucleic acid template comprises a recombination site, the generated concatamer will have a plurality of the recombination sites. The reaction of the concatamer having recombination sites with a recombination protein yields multiple copies of circular nucleic acids (mini-circles; pUC/loxP-RCA/Cre).

In a typical amplification reaction, 1 pg of plasmid DNA (DNA template) was amplified by RCA using Illustra™ TempliPhi™ DNA Amplification Kit (GE Healthcare, Piscataway, N.J., USA). The kit comprises a sample buffer, a reaction buffer, and an enzyme mix. The sample buffer comprises random hexamers that prime the DNA synthesis nonspecifically, and is used to denature the DNA template. The reaction buffer comprises salts and deoxyribonucleotides, and is maintained at a pH that is suitable for DNA synthesis. The enzyme mix comprises Phi29 DNA polymerase and random hexamers in 50% (v/v) glycerol. Manufacturer's instructions in the kit were followed for the DNA template amplification reaction.

Briefly, for an amplification reaction, 1 pg of purified plasmid DNA template (in a maximum of 1 µL) was added to 5 µL of the sample buffer to form a sample mixture. The sample mixture was heated to 95° C. for three minutes to denature the plasmid DNA template. The sample mixture was then cooled in an ice bath. To the sample mixture, 5 µL of the reaction buffer and 0.2 µL of the enzyme mix were added to form a reaction mixture. The reaction mixture was incubated at 30° C. for about 4 hours to about 18 hours. At the end of the incubation, the Phi29 DNA polymerase in the reaction mixture was inactivated by heating the reaction mixture at 65° C. for 10 minutes. At the end of the inactivation reaction, 90 mL water was added to the reaction mixture, and mixed well.

A control amplification reaction was conducted employing the plasmid vector pUC18 using the exact protocols as mentioned above, except that the enzyme mix (0.2 µL) was not added to the reaction mixture during the control amplification reaction.

The amplified plasmid DNA (pUC18-RCA, pUC/loxP-RCA) or mock-amplified plasmid DNA (pUC18-circular) was quantitated using Picogreen dsDNA quanitification assay (Molecular Probes Inc.). Agarose gel electrophoresis of the restricted DNA products was also performed, and the intensity of the electrophoresis bands was compared to those of standards having known concentration of DNA.

Each of the amplified nucleic acids (1 µL of pUC18-RCA or pUC/loxP-RCA) was incubated with Cre recombinase (1 unit of Cre recombinase in 1×Cre reaction buffer; 50 mM Tris-HCl, 33 mM NaCl, 10 mM $MgCl_2$, pH=7.5 at 25° C.) in a total volume of 5 µL for 1 h. at 37° C. The incubated samples (pUC18-RCA/Cre or pUC/loxP-RCA/Cre) were kept on ice till further use.

Bacterial transformation efficiency of the amplified plasmid DNA (pUC18-RCA, pUC/loxP-RCA or pUC18-circular), Cre recombinase treated amplified plasmid DNA (pUC18-RCA/Cre or pUC/loxP-RCA/Cre), and purified, unamplified pUC18-circular DNA was estimated using competent cells FB5α (Fisher Scientific) or NM522 (Protein Express Inc. Cleveland, Ohio, USA). In a typical transformation experiment, diluted DNA sample (60 ng/µL) in HET buffer (10 mM HEPES, 0.1 mM EDTA, 0.01% tween-20, pH=8.0 at 25° C.) was used for bacterial transformation with chemically competent cells to produce transformed cells. Manufacturer's recommendations were followed for transformation reaction. The transformed cells were grown overnight at 37° C. on LB plates under amplicillin selection. The transformation efficiency was quantified for each of the DNA samples as the average number of transformants/µg of DNA in duplicate samples.

Figure 3:
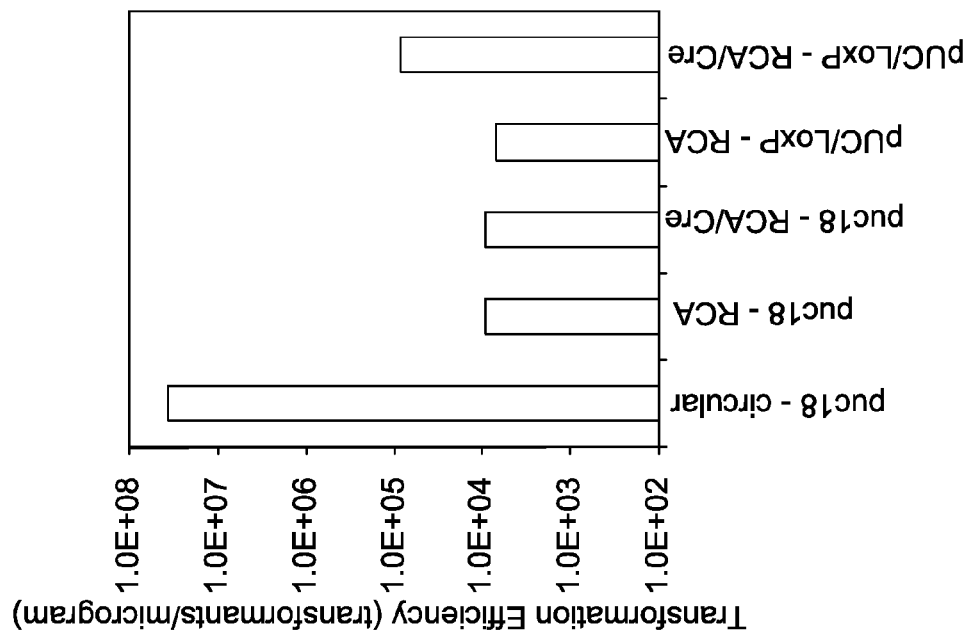
FIG. 3 shows the transformation efficiency of a nucleic acid generated according to one embodiment of the invention in FB5α cells.
Figure 2:
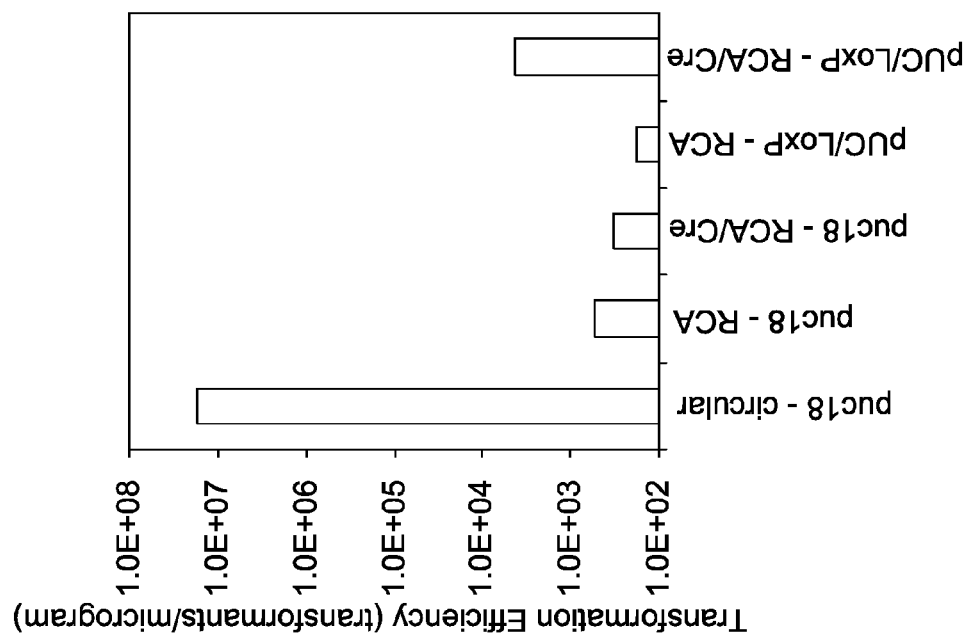
FIG. 2 shows the transformation efficiency of a nucleic acid generated according to one embodiment of the invention in NM522 cells.

FIG. 2 and FIG. 3 illustrate the transformation efficiency of the above DNA samples in NM522 cells and FB5α cells respectively. FIG. 2 illustrates that the concatamers (RCA products: pUC18-RCA or pUC/loxP-RCA) when directly transformed into NM522 yielded about 10,000-fold lower transformation efficiency than the superceded pUC18 control. The transformation efficiency of the pUC18-RCA was not affected significantly upon incubation with Cre recombinase. In contrast, treatment of the pUC/loxP-RCA with Cre-recombinase (pUC/loxP-RCA/Cre) increased the transformation efficiency significantly. About 10 to about 20-fold increase in transformation efficiency was observed upon incubation of the amplification product pUC/loxP-RCA with the Cre recombinase.

FIG. 3 illustrates that, the concatamers (RCA products: pUC18-RCA or pUC/loxP-RCA) when directly transformed into FB5α yielded about 1,000-fold lower transformation efficiency than the purified pUC18-circular controls. The transformation efficiency of the pUC18-RCA was hot significantly affected upon incubation with Cre recombinase. In contrast, treatment of the pUC/loxP-RCA with Cre-recombinase (pUC/loxP-RCA/Cre) increased the transformation efficiency significantly. About 10 to about 20-fold increase in transformation efficiency was observed upon incubation of the amplification product, pUC/loxP-RCA with the Cre recombinase.

The concatamers (RCA products) transformed competent E. coli well enough to yield ample numbers of colonies (tens to hundreds). However, the transformation efficiency of these concatamers was only about $10^{-3}$ to about $10^{-5}$ of that of a pure plasmid DNA, when normalized to the quantity of DNA applied. In this example, the amount of original plasmid DNA template carried over into the transformation mixture was considerably below than what was necessary to transform bacterial cells successfully. In the control transformations using mock-amplified pUC18, no bacterial transformants were obtained. It must be the concatamer product that was being transformed into the bacteria in these experiments, and not the input template DNA itself. The increase in transformation efficiency of the recombinase-treated, pUC/loxP-RCA product, and not the recombinase-treated, pUC18-RCA product was evidence that there was circularization of the DNA as a result of the recombinase treatment.

The foregoing examples are illustrative of some features of the invention, and are selected embodiments from a manifold of all possible embodiments. The invention may be embodied in other specific forms without departing from the spirit or essential characteristics thereof. While only certain features of the invention have been illustrated and described herein, one skilled in the art, given the benefit of this disclosure, will be able to make modifications/changes to optimize the parameters. The foregoing embodiments are therefore to be considered in all respects as illustrative rather than limiting on the invention described herein. Where necessary, ranges have been supplied, and those ranges are inclusive of all sub-ranges there between.

What is claimed is:

1. A method for generating a circular nucleic acid, comprising:
   providing a nucleic acid template, wherein the nucleic acid template comprises a single recombination site;
   amplifying the nucleic acid template to form a tandem repeat nucleic acid sequence, comprising multiple recombination sites; and
   generating multiple circular nucleic acids by incubating the tandem repeat nucleic acid sequence with a recombination protein in a cell-free system, wherein the recombination protein is chosen from a Cre recombinase, a bacteriophage lambda integrase, or a bacterial XerCD recombinase, and wherein each of the generated circular nucleic acids comprises a single recombination site.

2. The method of claim 1, wherein the recombination site is a site-specific recombination site.

3. The method of claim 1, wherein the recombination site is a loxP site.

4. The method of claim 1, wherein the recombination protein is a Cre recombinase from bacteriophage P1.

5. The method of claim 1, further comprising incubating the generated circular nucleic acid with an exonuclease.

6. The method of claim 5, wherein the exonuclease is chosen from an exonuclease I, an exonuclease III, or combinations thereof.

7. The method of claim 1, further comprising incubating the generated circular nucleic acid with a single-stranded DNA-binding protein.

8. The method of claim 1, further comprising transforming the generated circular nucleic acid to a prokaryotic cell.

9. The method of claim 1, further comprising transfecting the generated circular nucleic acid to a eukaryotic cell.

10. A method for generating circular nucleic acids in a cell-free system, comprising:
    providing a circular nucleic acid template, wherein the circular nucleic acid template is engineered to comprise a single recombination site;
    amplifying the circular nucleic acid template by rolling circle amplification to form a concatamer comprising multiple recombination sites, wherein the concatamer comprises tandem repeat units of the circular nucleic acid template sequence; and
    generating multiple circular nucleic acids by incubating the concatamer with a recombination protein, wherein the recombination protein is chosen from a Cre recombinase, a bacteriophage lambda integrase, or a bacterial XerCD recombinase, and wherein each of the generated circular nucleic acids comprises a single recombination site.

11. The method of claim 10, wherein the rolling circle amplification comprises incubating the circular nucleic acid template with a primer and a Phi29 DNA polymerase in the presence of deoxyribonucleoside triphosphates.

12. The method of claim 10, wherein the recombination site comprises SEQ ID NO: 1.

13. The method of claim 10, wherein the recombination protein is a Cre recombinase from bacteriophage P1.

14. The method of claim 10, further comprising processing the circular nucleic acids to generate a nucleic acid vaccine.

15. A method for generating a nucleic acid vaccine, comprising:
    providing a nucleic acid template, wherein the nucleic acid template comprises a single recombination site;
    amplifying the nucleic acid template to form a tandem repeat nucleic acid sequence, comprising multiple recombination sites; and
    generating the nucleic acid vaccine by incubating the tandem repeat nucleic acid sequence with a recombination protein, wherein the recombination protein is chosen from a Cre recombinase, a bacteriophage lambda integrase, or a bacterial XerCD recombinase, wherein each of the generated nucleic acid vaccine comprises a single recombination site.

16. The method of claim 15, wherein the nucleic acid template further comprises an expression cassette.

* * * * *

SEQUENCE LISTING

<160> NUMBER OF SEQ ID NOS: 1

<210> SEQ ID NO 1
<211> LENGTH: 34
<212> TYPE: DNA
<213> ORGANISM: Bacteriophage P1

-continued

```
<400> SEQUENCE: 1
ataacttcgt ataatgtatg ctatacgaag ttat                    34
```